United States Patent [19]

Smith et al.

[11] Patent Number: 5,228,776
[45] Date of Patent: Jul. 20, 1993

[54] APPARATUS FOR EVALUATING THERMAL AND ELECTRICAL CHARACTERISTICS IN A SAMPLE

[75] Inventors: Walter L. Smith, Livermore; Clifford G. Wells, Pleasanton; Allan Rosencwaig, Danville, all of Calif.

[73] Assignee: Therma-Wave, Inc., Fremont, Calif.

[21] Appl. No.: 879,760

[22] Filed: May 6, 1992

[51] Int. Cl.⁵ .......................................... G01N 25/72
[52] U.S. Cl. .......................................... 374/5; 374/7; 356/237
[58] Field of Search ........................ 374/4, 5, 6, 7; 356/237

[56] References Cited

U.S. PATENT DOCUMENTS

| | | | |
|---|---|---|---|
| 3,222,917 | 12/1965 | Roth | 374/5 |
| 3,413,474 | 11/1968 | Freeh | 374/7 |
| 3,451,254 | 6/1969 | Maley | 374/5 |
| 4,521,118 | 6/1985 | Rosencwaig | 374/5 |
| 4,522,510 | 6/1985 | Rosencwaig et al. | 374/7 |
| 4,551,030 | 11/1985 | Luukkala et al. | 374/7 |
| 4,579,463 | 4/1986 | Rosencwaig et al. | 374/57 |
| 4,634,291 | 1/1987 | Bantel et al. | 374/7 |
| 4,636,088 | 1/1987 | Rosencwaig et al. | 374/5 |
| 4,679,946 | 7/1987 | Rosencwaig et al. | 374/5 |
| 4,854,710 | 8/1989 | Opsal et al. | 356/432 |
| 5,042,952 | 8/1991 | Opsal et al. | 356/432 |

FOREIGN PATENT DOCUMENTS 0171441  9/1985  Japan ...................................... 374/4

Primary Examiner—William A. Cuchlinski, Jr.
Assistant Examiner—Diego F. F. Gutierrez
Attorney, Agent, or Firm—Limbach & Limbach

[57] ABSTRACT

An apparatus is disclosed for evaluating thermal and electrical characteristics of a sample. An intensity modulated pump beam is focused onto the surface of a sample at one spot. A non-modulated probe beam is focused onto the sample at a second spot, spaced laterally and vertically from the first spot. The distance between the two spots is at least two microns. The modulated power of the reflected probe beam that is in phase with the pump beam modulation frequency is monitored to provide information about the characteristics of the sample. The apparatus is particularly useful in evaluating the integrity of metal lines and vias in a semiconductor sample.

23 Claims, 3 Drawing Sheets

APPARATUS FOR EVALUATING THERMAL AND ELECTRICAL CHARACTERISTICS IN A SAMPLE

TECHNICAL FIELD

An apparatus is disclosed for evaluating thermal and electrical characteristics in a sample. The device is particularly useful in evaluating the integrity of metalized lines and vias in a semiconductor.

BACKGROUND OF THE INVENTION

There has been considerable interest in developing high resolution, non-destructive, non-contact techniques for evaluating samples. The need is particularly acute in the semiconductor industry where feature sizes are often in the micron and submicron range.

The assignee herein has developed one such device which is marketed under the trademark Thermaprobe Imager. The operation of this device is described in the following United States Patents which are hereby incorporated by reference: U.S. Pat. Nos. 4,521,118; 4,522,510; 4,636,088; 4,579,463; 4,854,710; 4,952,063 and 5,042,952.

All of the devices described in the above cited patents include a means for periodically exciting the sample at a highly localized spot on the sample surface. In the commercial embodiment of the device, this means is defined by an intensity modulated pump beam from an argon laser which is focused to a spot size of about one micron on the sample surface. The pump beam functions to periodically heat the sample which, in turn, generates thermal waves that propagate from the irradiated spot. In a semiconductor sample, the pump beam also functions to create an electron-hole plasma which propagates in a manner analogous to a thermal wave. Both the thermal and plasma waves interact with boundaries and barriers which scatter and reflect the waves. Features at or beneath the sample surface can be studied by monitoring the variations they induce in these waves.

As described in the cited patents, the thermal or plasma waves can be detected using a non-modulated probe beam of radiation. The probe beam is focused within the area on the sample surface which has been periodically excited. In one approach, the periodic angular displacements of the reflected probe beam, which are a result of the periodic angular changes in the surface of the sample, are monitored. In an alternate approach better suited to semiconductor samples, the periodic changes in the power of the reflected probe beam, which are a result of the changes in the optical reflectivity of the sample, are monitored. A third approach would include the use of an interferometer configuration for monitoring the periodic changes in the height of the sample surface within the periodically heated region. In each of these approaches, a phase sensitive detection system is used to monitor changes which are synchronous with the modulation frequency of the pump beam.

As described in the above cited patents, when the optical reflectivity of the sample is to be monitored, it is desirable to arrange the pump and probe beams to be coincident on the sample. This configuration helps to maximize the modulated power signal. In contrast, when the angular deflection of the beam is to be monitored, the pump and probe beams are separated a short distance, on the order of one to two microns. This separation functions to maximize the deflection signal.

FIG. 1 is a graph illustrating the signal strength which is available as a function of the distance from the center of the periodically heated spot C. As can be seen from curve 10, the modulated optical reflectivity signal is at maximum at the center of the heated spot and drops off rapidly as the distance from the heated spot increases. This sensitivity pattern would be the same for an interferometric detection system used to monitor periodic changes in the height of the sample due to the periodic heating. Curve 12 illustrates the signal available when measuring the angular deviations of the reflected probe beam. This signal is essentially zero at the center of the heated spot, increases and then once again decreases as the distance from the center of the spot C increases.

The scale of FIG. 1 is dependent on factors such as the thermal conductivity, specific heat and density of the sample as well as the modulation frequency of the pump beam. For a typical semiconductor sample and a modulation frequency on the order of 1 Mhz, the maximum signal strength represented in curves 10 and 12 will be attenuated by approximately 90% at a distance of 2 microns from the center of the periodically excited spot C. Even though the periodically excited region extends beyond two microns, it did not previously appear reasonable to operate with the probe beam separated from the pump beam a distance of more than two microns since the signal strength in that region is so highly attenuated. As will be discussed below, for certain samples, separating the pump and probe beams a distance of two microns or more has some unexpected benefits.

Metalized Lines and Vias in Semiconductors

Semiconductor components consist of a plurality of very small, discrete devices which are electrically interconnected by conductive metal lines. The interconnecting pattern of metalized lines is formed with standard deposition, masking and etching steps. The most common conductive metal employed is aluminum, but other metals such as tungsten, copper, titanium and metal silver compounds are also used.

In any given metalized layer, there will be a pattern of laterally extending (horizontal) conductive lines. Most present day semiconductor components have multiple levels and a method of connecting the lines between the levels must be employed. FIG. 2 illustrates a cross section of a portion of a two layer semiconductor device 20. Metal line 22 is formed on a lower layer and metal line 24 is formed on an upper layer. The lines are typically about one micron in width. A vertical interconnect or via 26 electrically connects the two metal lines.

As part of the semiconductor fabrication process, the integrity of the lines and particularly the vias must be explored. Various problems (shown schematically as 28, 30) related to factors such as incomplete deposition and electromigration result in cracks and voids in the metal lines. Because of the corners found in vias, the vias themselves are most susceptible to faulty formation.

One prior approach used for testing the lines and the vias involves selectively placing fine probe tips on the lines and measuring resistivity. A higher than expected resistivity measurement is indicative of cracks or voids somewhere in the metal pattern. The latter mechanical approach has a number of disadvantages. For example, the probes tips must make actual contact with the sample. In addition, a high resistance measurement can come from one or more defective vias and this method does not provide a good way of isolating the location of the problem. Typically, some form of destructive testing is needed to locate the problem.

As noted above, the assignee's Thermaprobe Imager device is a non-contact technique. However, identification of defective vias has been hampered because the surfaces associated with defective vias are often not optically flat, as indicated schematically at 28 in FIG. 2. More particularly, the surfaces can be dimpled, angled, rough or otherwise geometrically distorted and therefore tend to scatter light making reflected power measurements difficult. The detection system in the Thermaprobe Imager has the capability to monitor the periodic changes in the phase of the probe beam thereby minimizing the effects of scattering. However, in most cases, phase measurements are less desirable than modulated power measurements since the power measurements have a greater dynamic range.

Accordingly, it is an object of the subject to provide an improved method and apparatus for evaluating the integrity of vias.

It is a further and broader object of the subject invention to provide a method and apparatus for evaluating the thermal and electrical characteristics in a sample.

It is another object of the subject invention to provide a method of modifying an existing apparatus to improve the detection of surface and subsurface features in a sample.

SUMMARY OF THE INVENTION

In accordance with these and many other objects, the subject invention provides for a device which includes a means for generating a localized periodic excitation on a spot on the surface of the sample. In the preferred embodiment, the localized periodic excitation is created by an intensity modulated pump laser beam. The pump beam is focused to a spot size on the order of one micron. In the subject method of evaluating the integrity of vias, the pump beam is focused on the surface of a metalized line.

The pump beam generates thermal waves that travel through the sample. In the case of metalized lines, the thermal waves will be channeled or guided along the lines so that the transmission of the energy along the line will be greater than through the bulk metal.

In accordance with the subject invention, the transmitted signals are detected using a non-modulated probe beam which is focused on the surface of the sample at a second spot, spaced from the first spot. In a patterned wafer with metalized lines, the distance between the first and second spots is two microns or greater and the second spot is also located on a metal line.

The above described measurement configuration provides a number of advantages. First, both the pump and probe beams can be focused on optically flat surfaces even if there are intermediate geometrically distorted surfaces associated with a defect. Second, the thermal wave signal which does reach the displaced probe beam will have passed almost entirely through the region of interest, namely the metalized line. Thus, any defects in the line will have a major influence on the transmitted signal. Third, and as noted above, since the energy is being channelled by the line, the signal strength will be greater at the second spot than it would normally be at that distance from the pump beam spot. The transmission distance can be further increased by reducing the modulation frequency of the pump beam. The combination of factors listed above allows any defects in the metal line between the two spots to be easily detected.

In the preferred embodiment, changes in optical reflectivity of the sample are measured by monitoring the periodic changes in the modulated power of the reflected probe beam. In the alternative, periodic changes in the modulation of the phase of the reflected probe beam can be measured. Other detection schemes which rely on monitoring surface displacements can also be used. The latter schemes include interferometry and the measurement of angular deviations of the probe beam.

The existing commercial embodiment of the Thermaprobe Imager includes a means for controlling the separation between the pump and probe beams. This means has been provided to insure that the beams could be coincidently focused when measuring optical reflectivity, and spaced apart, by about one micron, when measuring the angular deviations of the probe beam. This same mechanism can be used to further separate the beams by two microns or more to perform the method of the subject invention.

In the preferred embodiment of the subject invention, the prior device would be further modified to provide an lens system for independently adjusting the focal plane of the pump and probe beams. By this arrangement, the pump beam can be focused on a metal line in one layer while the probe beam is focused on a line in a different layer. Using this approach, it can be relatively easy to find a flaw in a via which is used to connect the two lines.

While the subject method provides a highly beneficial solution for evaluating the integrity of metalized lines and vias, it can be used in other more general situations. More specifically, the subject invention can be used to evaluate any laterally extending region in a sample that has a higher thermal conductivity than the surrounding regions and therefore acts to channel the energy beyond the pump beam spot. In this case, there will be sufficient signal at a second spot, which is laterally displaced from the first spot, so that detection is possible. This approach can be used to evaluate the integrity of that laterally extending region.

As noted above, the energy transfer through the metal lines is typically in the form of thermal waves. Thus, changes in the signal can be attributed to variations in thermal conductivity along the path. It should also be noted that thermal conductivity is related to electrical conductivity by the Wiedemann-Franz law. Thus, the subject approach can be used to monitor variations in electrical conductivity and resistance of the sample as well.

Further objects and advantages of the subject invention will become apparent from the following detailed description taken in conjunction with the drawings in which:

DETAILED DESCRIPTION OF THE PREFERRED EMBODIMENT

Figure 3:
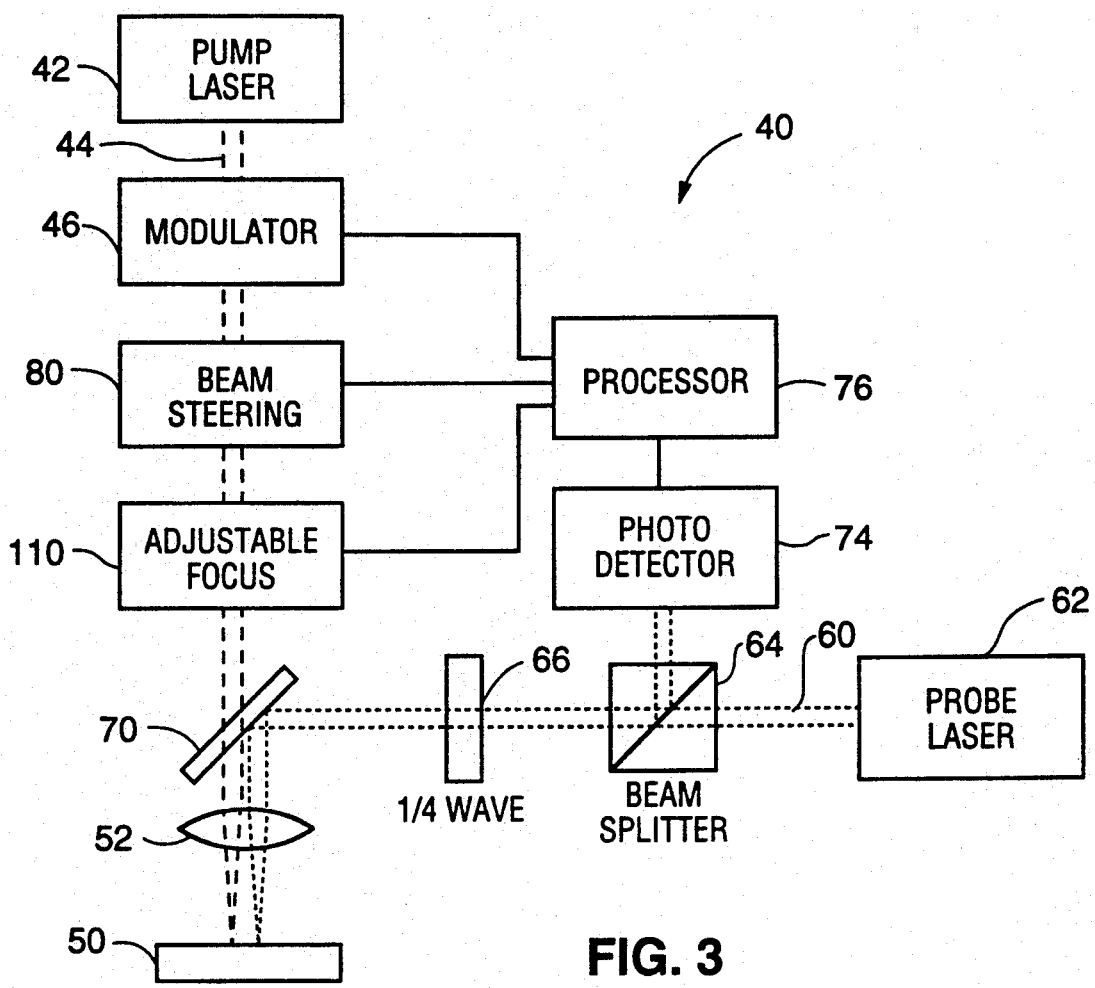
FIG. 3 is a schematic diagram illustrating the apparatus of the subject invention.

Referring to FIG. 3, there is illustrated a schematic diagram of the apparatus 40 for performing the method of the subject invention. FIG. 3 illustrates the basic components of the apparatus. The preferred embodiment is substantially similar to the assignee's Thermaprobe Imager with the modifications discussed in greater detail below.

Apparatus 40 includes a laser 42 for generating a pump beam 44 of radiation. Laser 42 may be an argon laser having a CW output of several milliwatts. The pump beam 44 is passed through an acousto-optic modulator 46 for intensity modulating the pump beam. The chopping frequency should be greater than 50 kHz.

The intensity modulated pump beam 46 is focused onto the surface of the sample 50 surface by a spherical microscope objective 52 to a diameter of one micron or less. In the preferred embodiment, microscope objective 52 has a numerical aperture of 0.95 and functions to focus the beam to a spot size of 0.5 microns in diameter. The intensity of the beam at the surface of the sample is at least $10^4$ watts/cm$^2$.

As described in the above cited patents, the intensity modulated argon pump beam functions to periodically excite the sample. The excitation radiation could be supplied by other wavelengths including X-rays, gamma rays, infrared, ultraviolet, microwave or radio frequencies. The periodic excitation could also be created by an intensity modulated stream of particles such as electrons, protons, neutrons, ions or molecules. Further, periodic resistive heating could also be electrically generated at a point source in the sample.

The periodic excitation from the pump beam will generate thermal and/or plasma waves which propagate radially from the center of the focused spot. The distance which the waves propagate will be dependent on sample parameters and the modulation frequency. By focusing a probe beam of radiation within the periodically excited region, information about the sample can be evaluated.

In the preferred embodiment, the probe beam 60 is generated by a Helium-Neon laser 62. The probe beam 60 is passed through a polarizing splitter 64 and a quarter-wave plate 66. The probe beam 62 is then turned downwardly by dichroic mirror 70. The probe beam is focused onto the sample surface by spherical lens 52 to a spot size of one micron or less.

The reflected probe beam 60 is returned through quarter-wave plate 66. The two passes through the quarter-wave plate function to rotate the polarization of the beam by ninety degrees so that it will be reflected upwardly by splitter 64. The probe beam is then received by photodetector 74. The beam is arranged to underfill the surface of the detector. Detector 74 is preferably a quad cell detector. The power of the reflected probe beam is determined by adding all four quadrants of the detector. Angular deviations of the probe beam can be determined by computing the difference signal measured in opposite halves of the detector. Details of these measurements are set forth in the above cited patents.

The output of detector 74 is supplied to processor 76. Processor 76 is also connected to the modulator 46. The processor is arranged to provide phase sensitive detection so that changes in the modulated probe beam that occur at the modulation frequency of the pump beam are analyzed as opposed to absolute changes in the beam.

In the commercial embodiment of the Thermaprobe Imager, additional elements are provided which have not been illustrated in FIG. 3 since they are not essential to an understanding of the subject invention. For example, various additional photodetectors are provided to monitor changes in the output of the pump and probe beam lasers. These detectors are used to normalize the signals measured by detector 74. In addition, an autofocus system is provided to accurately maintain the sample in the focal plane of the probe beam to maximize resolution. Various filters are provided to screen the detectors from unwanted light. The Thermaprobe Imager also includes a white light source, the output of which is focused through the objective 52 onto the sample. The returning white light is imaged by a video camera to allow the operator to view the surface of the sample to aid in positioning and the interpretation of data.

The commercial embodiment also includes a variety of beam steering optics for both the pump and probe beams. One set of those optics 80 is illustrated schematically in FIG. 3. This set of steering optics is electronically controlled and has been used to vary the position of the pump beam with respect to the probe beam. The steering optics includes a pair of rotatable plates (not shown) for adjusting the position of the beam in two perpendicular planes. The beam is then passed through a collimator (not shown). When the plates are adjusted to pass the beam down the center of the collimator, the beam will exit the collimator parallel to its longitudinal axis. This beam will then be focused on the sample along the center line of the objective 52.

If the rotatable plates are adjusted such that the beam enters the collimator coaxial to, but spaced from its center axis, the beam will exit the collimator at an angle. A beam entering the lens 52 at an angle will be focused onto the surface of the sample at a point spaced from the center line of the lens.

In the prior device, the steering optics 80 were used to control the relative lateral positions of the pump and probe beam spots on the surface of the sample. More particularly, if the reflected power of the probe beam was to be measured, the steering optics were adjusted so that the pump and probe beam spots were coincident on the sample. In contrast, if the angular deviations of the probe beam was to be measured, the steering optics were adjusted so that the pump and probe beam spots were spaced apart a distance of about one micron.

Figure 4:
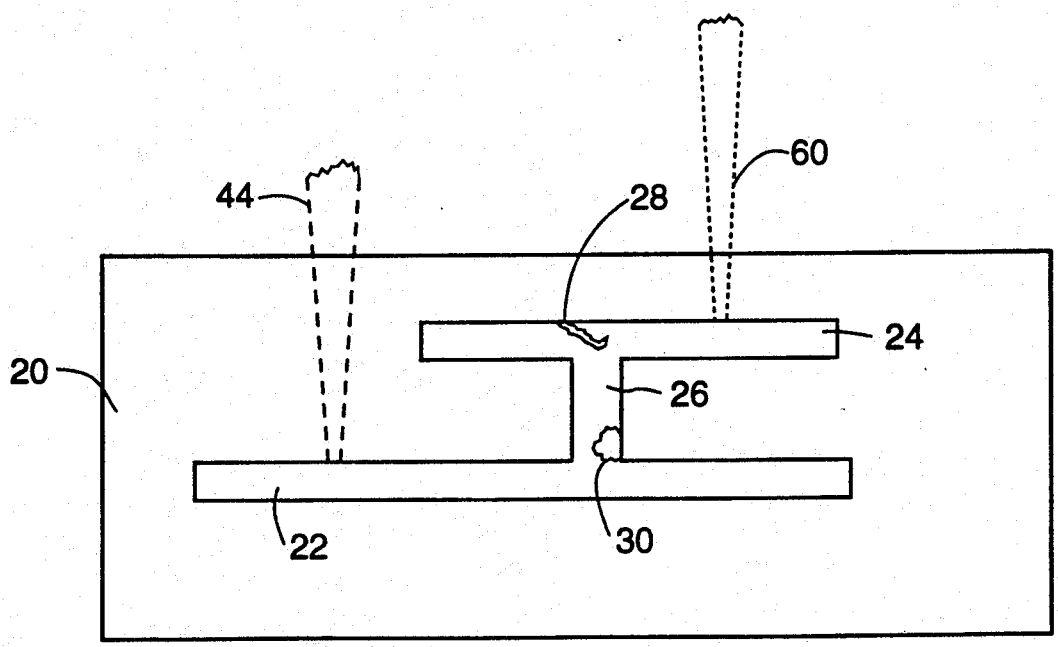
FIG. 4 is a view, similar to FIG. 2, showing the pump beam and the displaced probe beam focused on two metal lines.

In accordance with the subject invention, the steering optics 80 are adjusted so that the distance between the pump and probe beam spots is further increased and is preferably at least two microns. FIGS. 4 and 5 illustrate situations where this increased separation between the pump and probe beams would be desirable.

Figure 2:
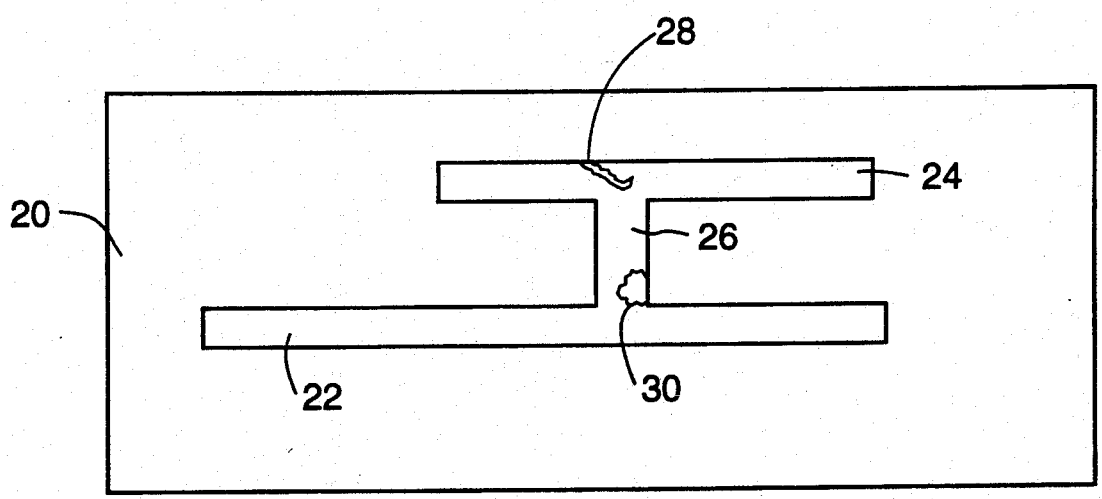
FIG. 2 is a simplified cross section of two metals lines formed on different layers in a semiconductor and the interconnecting via.

FIG. 4 is an illustration similar to FIG. 2 with like numbers indicating like features. As can be seen, the pump beam 44 is focused on one metal line 22. The probe beam is focused on a second metal line 24. In operation, the periodic heating generated by the pump beam 44 will spread out through the sample. Because the thermal conductivity of the metal lines is so much greater than the surrounding sample, the heat flow will be laterally guided along the metal lines. The periodic heating of line 24 can be detected by probe beam 60.

Figure 5A:
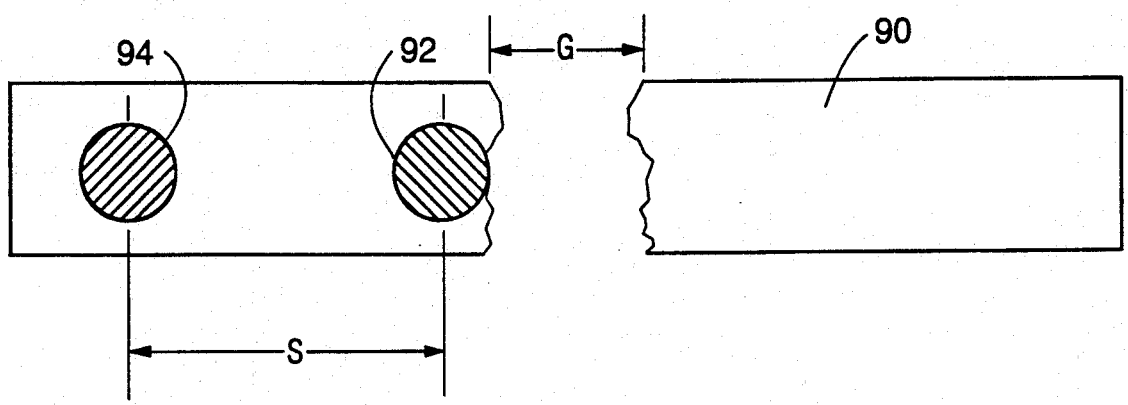
FIGS. 5a and 5b illustrate the signal which would be measured from the probe beam as the pump and probe beams are scanned over a crack in a metal line.
Figure 5B:
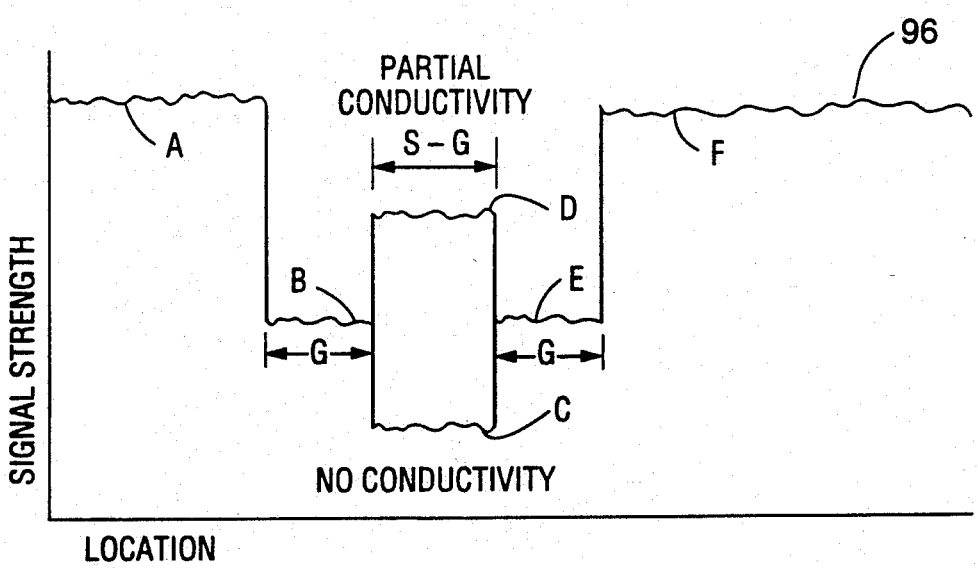

It has been found that the strength of the signal available at the displaced probe beam spot will be severely degraded if there are faults in the lines or vias between the pump and the probe beams. This phenomenon is illustrated in FIG. 5. FIG. 5a illustrates a top plan view of a metal line 90. Line 90 has a defect or gap G in the middle. The pump and probe beam spots 92, 94 are illustrated in a starting position on the left side of the line structure. The modulated reflected power of the probe beam measured by detector 74 is illustrated in FIG. 5b. The curve 96 is an example of the output signal which would be generated as the pump and probe beams are scanned along the metal line 90, from left to right, maintaining a separation S between the spots. The signal is generated from the probe beam location.

As can be seen from region A of curve 96 in FIG. 5b, when both the pump and probe beam spots are on a solid metal line with no flaws, the output signal is at a maximum. As the beam spots are scanned in tandem and the pump beam spot 92 hits the flaw G, the signal will drop significantly as illustrated by region B of curve 96. In this region, the energy from the pump beam is being highly scattered such that only a small portion of the energy is transferred into the sample. It should be noted that the signal will drop even though the probe beam spot 94 is still located on a good portion of the line. Thus, a drop-off in signal does not necessarily indicate a problem at the location of the probe beam spot.

As the tandem scan of the spots continues, a position will be reached when both the pump and probe beam spots will be straddling the defect. This position is ideal for detecting a problem. More particularly, both the pump and probe beam spots are located on smooth metal surfaces. Therefore, all the energy of the pump beam can be transferred into the line. Furthermore, the detection of the modulated power of the reflected probe beam will not be adversely effected by scattering. If the flaw G in the line is a complete void, the signal strength will drop even further as indicated by region C on curve 96. On the other hand, if the flaw is only a partial break (the more common occurrence), the signal strength will increase as shown by region D on curve 96.

As the beam spots are scanned further, the probe beam spot will strike the defect G while the pump beam will move back onto a good portion of the metal line. The signal strength in this region E will be similar to region B since the probe beam will be scattered. The signal strength will return to maximum in region F when both beam spots are back on the solid metal line.

The signal pattern shown in FIG. 5 demonstrates how a very simple approach can be developed for evaluating the integrity of the lines and vias in a semiconductor sample. More particularly, the processor can be programmed to scan the displaced beam spots over the lines in the sample. This scanning can be accomplished automatically with known wafer pattern recognition systems. A template can be stored which maps the expected signal strengths of properly formed lines and vias as a function of position on a sample. Any significant deviation in signal strength from the stored template will indicate a defective line or via. Since the beams are being focused to micron size spots and the separation is on the order of two to three microns, the location of the problem can be accurately determined. As noted above, a drop in signal will indicate that a defect exists between the two beam spots.

As mentioned above, as an alternative to monitoring the modulated power of the probe beam, the periodic changes in the phase of the probe can also be monitored with the synchronous detection system. While this approach is less desirable in most measurement situations due to a decrease in the signal to noise ratio, it is insensitive to variations caused by scattering. Thus, where the surface of the test sample has significant geometric distortions, monitoring the periodic changes in the phase of the probe beam may be preferred. It should be noted that if the latter approach was used, the signal in regions B and E of FIG. 5B would appear the same as in regions A and F.

As discussed above with reference to FIG. 2, typical pattern wafer semiconductors have multiple layers with lines at different depths. The operation of the subject system can be improved if the focal plane of the two beams can be independently controlled. More particularly, and as shown in FIG. 4, line 22 is at a depth deeper than line 24. Since the material between the layers is typically an oxide which is essentially transparent to the pump and probe beams, one of the beams can be focused onto the lower line 22 while the other beam can be focused onto the upper line 24. Independent focusing allows maximum resolution (i.e. minimum spot size) to maintained.

In the commercial embodiment of the Thermaprobe Imager, an autofocus signal is derived from the reflected probe beam. Therefore, it would be preferable to provide an independent focal adjustment for the pump beam to avoid interfering with the autofocus system associated with the probe beam. A means for independently focusing the pump beam is shown schematically by numeral 110 in FIG. 3. Focusing system 110 will consist of an electrically controlled lens system whose position can be changed, varying the focus of the pump beam the desired amount.

During initial testing with metal lines and vias, it has been found the optimum detection can be obtained by measuring the periodic changes in optical reflectivity of the sample by measuring the modulated reflectance of the probe beam. Non-semiconductor samples may exhibit significant surface deformations which could be detected by other approaches. One approach, described in U.S. Pat. Nos. 4,521,118 and 4,522,510 relies on measuring the periodic changes in the angular deviations of the probe beam. As noted above, the measurement is made by computing a difference signal from the quad cell detector 74. Another technique would entail the use of an interferometer. An interferometer structure is described in U.S. Pat. No. 5,042,952.

Figure 1:
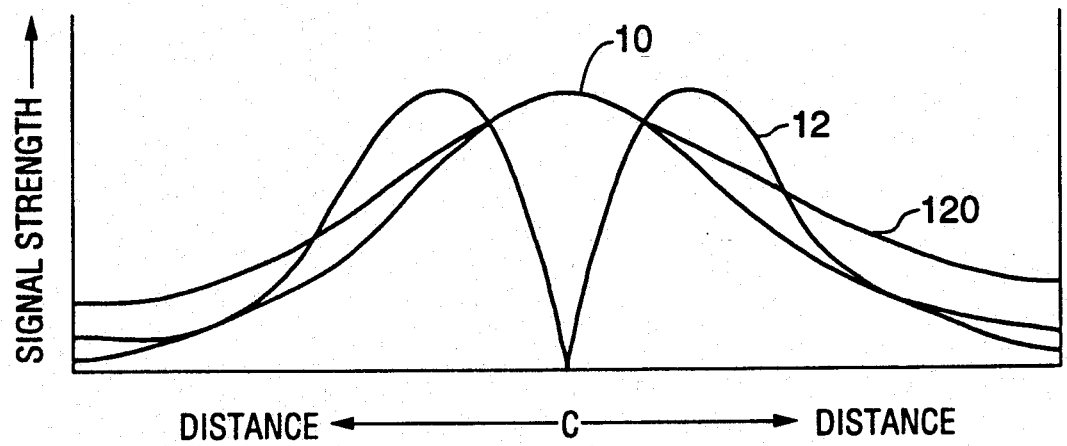
FIG. 1 is a graph which illustrates the variation in signal strength with respect to the distance from the center of the periodically excited spot.

To gain the benefits of the subject invention, the spacing between the pump and probe beam spots should be at least two microns. In the case of evaluating lines and vias, the features of interest are in the micron range and the beam spots should be separated sufficiently to straddle the defect. It has been found that when measuring on a one micron wide metal line, the signal strength available when the spots are separated in the two to three micron range is greater than it would be in a bulk metal. Curve 120 in FIG. 1 illustrates the increased lateral extent of the signal in this situation. Initial testing has been performed at a pump beam modulation frequency of 1 MHz. It is believed that the transmission distance of the signal can be further increased by lowering the modulation frequency of the pump beam thereby increasing the diffusion length of the thermal waves.

The subject method will have utility in any sample where a detectable signal can be obtained a significant distance from the pump beam. As noted above, by separating the beams, the signal detected at the probe beam will have passed through and been significantly affected by any intermediate feature. In this manner, sensitivity is increased. In addition, if the surface associated with a defect is geometrically distorted, the beams may be positioned to straddle the effected region, thereby minimizing scattering and improving signal strength.

The subject invention can also be used advantageously for the evaluation of electrical conductivity and resistivity in the samples. As can be appreciated, since the ratio of the thermal conductivity of a metal to its electrical conductivity is a constant times the absolute temperature (as given by the Wiedemann-Franz law), the system could also be employed in manner similar to an ohm meter on a micron scale. Information about electrical conductivity on this scale can be quite helpful in the design and manufacture of semiconductors.

While the subject invention has been described with reference to a preferred embodiment, various changes and modifications could be made therein, by one skilled in the art, without varying from the scope and spirit of the subject invention as defined by the appended claims.

We claim:

1. An apparatus for evaluating a sample comprising:
    means for generating a pump beam of radiation;
    means for intensity modulating the pump beam;
    means for focusing the pump beam on the sample at a first spot;
    means for generating a probe beam of radiation;
    means for focusing said probe beam at a second spot on said sample, said second spot being located within a region which has been periodically exited by the pump beam and being both laterally and vertically displaced from said first spot;
    means for monitoring the periodic variations in the probe beam after the probe beam has interacted with the sample, said monitored variations resulting from and being synchronous with the modulated pump beam; and
    processor means for evaluating the sample based on the monitored variations of the probe beam.

2. An apparatus as recited in claim 1 wherein said pump beam of radiation is generated by a laser.

3. An apparatus as recited in claim 2 wherein said pump laser beam is focused at said first spot with a diameter of one micron or less.

4. An apparatus as recited in claim 3 wherein said probe beam is focused at said second spot with a diameter of one micron or less.

5. An apparatus as recited in claim 4 wherein the spacing between said first and second spots is at least two microns.

6. An apparatus as recited in claim 1 wherein said monitoring means measures the modulated power of the probe beam.

7. An apparatus as recited in claim 1 wherein said monitoring means measures the periodic changes in the phase of the probe beam.

8. An apparatus as recited in claim 1 wherein said means for focusing said pump and probe beams is a lens through which both of said beams pass.

9. Am apparatus as recited in claim 8 further including beams steering means for controlling the separation between said first and second spots.

10. An apparatus as recited in claim 9 further including an adjustable focusing means in the path of one of said beams for independently focusing said one beam in a vertical plane different from the other beam.

11. An apparatus as recited in claim 1 wherein said pump beam has an intensity of at least $10^4$ Watts/cm$^2$ at the sample surface.

12. A method of evaluating the integrity of a via formed between and connecting two metalized lines on a semiconductor sample, said lines being formed in different horizontal layers in the sample, said method comprising the steps of:
    focusing an intensity modulated pump beam of radiation at a first spot on one of said lines;
    focusing a probe beam of radiation at a second spot, said second spot being on said second line and being both laterally and vertically displaced from said first spot;
    monitoring the periodic variations in the power of the probe beam after the probe beam has interacted with the sample, said periodic variations being in phase with the modulation frequency of the pump beam and resulting from changes in the optical reflectivity at the second spot; and
    evaluating the integrity of the via based on the monitored variations in the power of the probe beam.

13. A method as recited in claim 12 wherein the intensity modulated pump beam of radiation is generated by a laser.

14. A method as recited in claim 13 wherein said pump laser beam is focused at said first spot with a diameter of one micron or less.

15. A method as recited in claim 14 wherein said probe beam is focused at said second spot with a diameter of one micron or less.

16. A method as recited in claim 15 wherein the spacing between said first and second spots is at least two microns.

17. A method as recited in claim 12 wherein said pump and probe beams ar focused through a single lens.

18. A method for evaluating a sample comprising the steps of:
    generating a pump beam of radiation;
    intensity modulating the pump beam at a predetermined frequency;
    focusing the pump beam onto the surface of the sample at a first spot;
    generating a probe beam of radiation;
    focusing said probe beam at a second spot on said sample, said second spot being located within a region which has been periodically exited by the pump beam and being both laterally and vertically displaced from said first spot a distance of at least two microns;
    monitoring the periodic variations in the modulated power of the probe beam after the probe beam has interacted with the sample, said periodic variations being in phase with the modulation frequency of the pump beam and resulting from changes in the optical reflectivity of the sample; and
    evaluating the sample based on the monitored variations in the power of the probe beam.

19. A method as recited in claim 18 wherein the pump beam of radiation is generated by a laser.

20. A method as recited in claim 19 wherein said pump laser beam is focused at said first spot with a diameter of one micron or less.

21. A method as recited in claim 20 wherein said probe beam is focused at said second spot with a diameter of one micron or less.

22. A method as recited in claim 21 wherein the spacing between said first and second spots is at least two microns.

23. A method as recited in claim 18 wherein said pump and probe beams are focused through a single lens.

* * * * *